United States Patent
Mestayer et al.

(10) Patent No.: US 9,080,949 B2
(45) Date of Patent: Jul. 14, 2015

(54) DETECTING BROADSIDE AND DIRECTIONAL ACOUSTIC SIGNALS WITH A FIBER OPTICAL DISTRIBUTED ACOUSTIC SENSING (DAS) ASSEMBLY

(75) Inventors: Jeffery Joseph Mestayer, Kingwood, TX (US); Peter Berkeley Wills, Alberta (CA)

(73) Assignee: Shell Oil Company, Houston, TX (US)

( * ) Notice: Subject to any disclaimer, the term of this patent is extended or adjusted under 35 U.S.C. 154(b) by 496 days.

(21) Appl. No.: 13/518,083

(22) PCT Filed: Dec. 21, 2010

(86) PCT No.: PCT/US2010/061478
§ 371 (c)(1),
(2), (4) Date: Jun. 21, 2012

(87) PCT Pub. No.: WO2011/079107
PCT Pub. Date: Jun. 30, 2011

(65) Prior Publication Data
US 2013/0211726 A1    Aug. 15, 2013

Related U.S. Application Data

(60) Provisional application No. 61/289,469, filed on Dec. 23, 2009.

(30) Foreign Application Priority Data

Dec. 21, 2010 (EP) ..................................... 10196253

(51) Int. Cl.
*G02B 6/00* (2006.01)
*G01N 29/24* (2006.01)
*G01H 9/00* (2006.01)

(52) U.S. Cl.
CPC ........... *G01N 29/2418* (2013.01); *G01H 9/004* (2013.01); *G01N 2291/044* (2013.01)

(58) Field of Classification Search
None
See application file for complete search history.

(56) References Cited

U.S. PATENT DOCUMENTS 4,297,787 A    11/1981    Bucaro .......................... 73/655
4,297,887 A    11/1981    Bucaro
(Continued)

FOREIGN PATENT DOCUMENTS

GB    2197953 A  *  6/1988
GB    2364380        1/2002    .............. E21B 47/00
(Continued)

OTHER PUBLICATIONS

International Preliminary Report on Patentability for PCT/US2010/061478, dated Jun. 26, 2012.*

*Primary Examiner* — Mike Stahl

(57) ABSTRACT

A Distributed Acoustic Sensing(DAS) fiber optical assembly comprises adjacent lengths of optical fiber A, B with different directional acoustic sensitivities, for example by providing the first length of optical fiber A with a first coating 35, such as acrylate, and the second length of optical fiber B with a second coating 36, such as copper, wherein the first and second coatings 35 and 36 may be selected such that the Poisson's ratio of the first length of coated fiber A is different from the Poisson's ratio of the second length of coated fiber B. The different Poisson's ratios and/or other properties of the adjacent lengths of optical fiber A and B improve their directional acoustic sensitivity and their ability to detect broadside (radial) acoustic waves.

15 Claims, 2 Drawing Sheets

(56) References Cited

U.S. PATENT DOCUMENTS

| | | | |
|---|---|---|---|
| 4,363,114 A | 12/1982 | Bucaro et al. | |
| 4,405,198 A * | 9/1983 | Taylor | 385/13 |
| 4,427,263 A * | 1/1984 | Lagakos et al. | 385/128 |
| 4,525,818 A * | 6/1985 | Cielo et al. | 367/149 |
| 4,621,896 A | 11/1986 | Lagakos et al. | 350/96.29 |
| 4,979,798 A * | 12/1990 | Lagakos et al. | 385/12 |
| 5,093,880 A * | 3/1992 | Matsuda et al. | 385/100 |
| 5,373,487 A | 12/1994 | Crawford et al. | 367/149 |
| 5,841,529 A * | 11/1998 | Sirkis et al. | 356/481 |
| 5,870,194 A | 2/1999 | Cordova et al. | |
| 6,268,911 B1 | 7/2001 | Tubel et al. | 356/72 |
| 6,281,489 B1 | 8/2001 | Tubel et al. | 250/227.14 |
| 6,588,266 B2 | 7/2003 | Tubel et al. | 73/152.39 |
| 6,596,394 B2 | 7/2003 | Toler et al. | 428/392 |
| 6,787,758 B2 | 9/2004 | Tubel et al. | 250/227.14 |
| 7,040,390 B2 | 5/2006 | Tubel et al. | 166/64 |
| 7,201,221 B2 | 4/2007 | Tubel et al. | 166/64 |
| 7,277,162 B2 * | 10/2007 | Williams | 356/32 |
| 7,284,903 B2 | 10/2007 | Hartog | 374/130 |
| 7,668,411 B2 | 2/2010 | Davies et al. | 385/12 |
| 7,740,064 B2 | 6/2010 | McCoy et al. | 166/250.01 |
| 7,946,341 B2 | 5/2011 | Hartog et al. | 166/254.1 |
| 7,954,560 B2 | 6/2011 | Mathiszik et al. | 175/50 |
| 2002/0164141 A1 * | 11/2002 | Suhir | 385/128 |
| 2004/0043501 A1 | 3/2004 | Means et al. | 436/164 |
| 2009/0188665 A1 | 7/2009 | Tubel et al. | 166/250.1 |
| 2010/0107754 A1 | 5/2010 | Hartog et al. | 73/152.47 |
| 2010/0207019 A1 | 8/2010 | Hartog et al. | 250/269.1 |
| 2010/0254650 A1 * | 10/2010 | Rambow | 385/13 |
| 2010/0315630 A1 | 12/2010 | Ramos et al. | 356/301 |
| 2011/0069302 A1 | 3/2011 | Hill et al. | 356/73.1 |
| 2011/0088462 A1 | 4/2011 | Samson et al. | 73/152.18 |
| 2011/0088910 A1 | 4/2011 | McCann et al. | 166/344 |
| 2011/0149688 A1 | 6/2011 | Hill et al. | 367/87 |
| 2011/0185815 A1 | 8/2011 | McCann | 73/655 |
| 2011/0216996 A1 | 9/2011 | Rogers | 385/12 |
| 2011/0280103 A1 | 11/2011 | Bostick, III | 367/35 |
| 2011/0292763 A1 | 12/2011 | Coates et al. | 367/25 |
| 2012/0017687 A1 | 1/2012 | Davis et al. | 73/655 |
| 2012/0018149 A1 | 1/2012 | Fidan et al. | 166/250.03 |
| 2013/0291643 A1 * | 11/2013 | Lumens | 73/655 |

FOREIGN PATENT DOCUMENTS

| | | | |
|---|---|---|---|
| WO | 8804032 | 6/1988 | |
| WO | WO2009158630 | 12/2009 | G01N 21/00 |
| WO | WO2010010318 | 1/2010 | G01V 1/100 |
| WO | WO2010034986 | 4/2010 | G01M 3/04 |
| WO | WO2010136764 | 12/2010 | |
| WO | WO2010136810 | 12/2010 | G01D 5/343 |
| WO | WO 2011010110 | 1/2011 | G01D 5/353 |
| WO | 2011039501 | 4/2011 | |
| WO | 2011058312 | 5/2011 | |
| WO | 2011058313 | 5/2011 | |
| WO | 2011058314 | 5/2011 | |
| WO | 2011058322 | 5/2011 | |
| WO | 2011067554 | 6/2011 | |
| WO | 2011076850 | 6/2011 | |
| WO | 2011079107 | 6/2011 | |
| WO | 2011141537 | 11/2011 | |
| WO | 2011148128 | 12/2011 | |

* cited by examiner

DETECTING BROADSIDE AND DIRECTIONAL ACOUSTIC SIGNALS WITH A FIBER OPTICAL DISTRIBUTED ACOUSTIC SENSING (DAS) ASSEMBLY

RELATED CASES

This case is a national stage entry of PCT/US2010/061478 filed 21 Dec. 2010, which claims priority from U.S. Provisional Application 61/289,469, filed 23 Dec. 2009, and EP 10196253.8 filed 21 Dec. 2010, all of which are incorporated by reference.

FIELD OF THE INVENTION

The invention relates to fiber optic devices and in particular to a fiber optical Distributed Acoustic Sensing (DAS) assembly adapted to sense the magnitude and direction of acoustic signals that are travelling at an angle or substantially perpendicular to the device.

BACKGROUND OF THE INVENTION

Various attempts have been made to provide sensing capabilities in the context of petroleum exploration, production, and monitoring, with varying degrees of success. Recently, these attempts have included the use of fiber optic cables to detect acoustic energy. Because the cables typically comprise optically conducting fiber containing a plurality of backscattering inhomogeneities along the length of the fiber, such systems allow the distributed measurement of optical path length changes along an optical fiber by measuring backscattered light from a laser pulse input into the fiber. Because they allow distributed sensing, such systems may be referred to as "distributed acoustic sensing" or "DAS" systems. One use of DAS systems is in seismic applications, in which seismic sources at known locations transmit acoustic signals into the formation, and/or passive seismic sources emit acoustic energy. The signals are received at seismic sensors after passing through and/or reflecting through the formation. The received signals can be processed to give information about the formation through which they passed. This technology can be used to record a variety of seismic information. Another application range is concerning in-well applications.

While there exists a variety of commercially available DAS systems that have varying sensitivity, dynamic range, spatial resolution, linearity, etc., all of these systems are primarily sensitive to axial strain. As the angle between direction of travel of the acoustic signal and the fiber axis approaches 90°, DAS cables become much less sensitive to the signal and may even fail to detect it.

Thus, it is desirable to provide an improved cable that is more sensitive to signals travelling normal to its axis and enables distinguishing this radial strain from the axial strain. Such signals may sometimes be referred to as "broadside" signals and result in radial strain on the fiber. Sensitivity to broadside waves is particularly important for seismic or microseismic applications, with cables on the surface or downhole.

SUMMARY OF THE INVENTION

In accordance with the invention there is provided a Distributed Acoustic Sensing(DAS) fiber optical assembly comprising at least two lengths of adjacent optical fiber with different directional acoustic sensitivities. The at least two lengths of adjacent optical fiber may comprise a first length of optical fiber A with a first ratio between its axial and radial acoustic sensitivity and a second length of optical fiber B with a second ratio between its axial and radial acoustic sensitivity. The first ratio may be between 100 and 300 and the second ratio may be between 300 and 700.

The at least two lengths of adjacent optical fiber may comprise a first length of coated fiber having a first coating, such as an acrylate coating, and a second length of coated fiber may having a second coating, such as a copper coating, wherein the first and second coatings are selected such that the Young's Modulus or Poisson's ratio of the first length of coated fiber is less than the Young's Modulus or Poisson's ratio of the second length of coated fiber.

Alternatively or additionally the at least two lengths of adjacent optical fiber comprise a first length of optical fiber with a first diameter and a second length of optical fiber with a second diameter.

Optionally, the at least two lengths of adjacent optical fiber comprise adjacent sections of a single fiber optic cable having a coating with at least one property that varies along the length of the cable, the at least one property being selected from the group consisting of Poisson's ratio and Young's modulus.

In accordance with the invention there is furthermore provided a directionally sensitive Distributed Acoustic Sensing (DAS) method, which comprises deploying the Distributed Acoustic Sensing (DAS) assembly comprising at least two lengths of adjacent optical fiber with different directional acoustic sensitivities according to the invention.

In a preferred embodiment of the invention there is provided an improved fiber optical cable that is more sensitive to signals travelling normal to its axis.

Some embodiments of the invention include a fiber optic cable comprising a first fiber having a first coating and a second fiber having a second coating, wherein the first and second coatings are selected such that the Young's Modulus or Poisson's ratio of the first coated fiber is less than the Young's Modulus or Poisson's ratio of the second coated fiber. This fiber can be used to advantage in a method for creating an image of a subsurface, locating microseisms, or the like, or in-well. The method comprises the steps of a) deploying the fiber optic cable, b) transmitting a seismic signal into the subsurface, c) recording a first data set on the first fiber and a second data set on the second fiber, wherein the data sets include signals received as a result of the seismic signal in step b), d) adjusting at least a portion of the first data set with at least a portion of the second data set so as to obtain an output data set that is indicative of the portions of received signals travelling through the subsurface at either in an axial or radial direction with respect to the cable, and e) using the output data set to derive information about the subsurface or in-well conditions.

Other embodiments include a fiber optic cable comprising a fiber having a coating, wherein the coating has at least one property that varies along the length of the cable, wherein the property is selected from the group consisting of Poisson's ratio and Young's modulus. This fiber can be used to advantage in a method comprising the steps of: a) deploying the fiber optic cable, b) transmitting a seismic signal into the subsurface, c) recording a received data set on the fiber, said received data sets including signals received as a result of the seismic signal in step b), d) processing the received data set so as to obtain an output data set that is indicative of received signals having a broadside component or no broadside component with respect to the cable, and e) using the output data set to derive information about the subsurface.

Step a) may comprise deploying the cable in a deviated borehole. A portion of the borehole may be deviated at least 45 degrees from vertical and at least portion of the cable may be deployed in the deviated portion.

These and other features, embodiments and advantages of the Distributed Acoustic Sensing(DAS) fiber optical assembly and method according to the invention are described in the accompanying claims, abstract and the following detailed description of non-limiting embodiments depicted in the accompanying drawings, in which description reference numerals are used which refer to corresponding reference numerals that are depicted in the drawings.

BRIEF DESCRIPTION OF THE DRAWINGS

For a more detailed understanding of the invention, reference is made to the accompanying drawings wherein.

DETAILED DESCRIPTION OF A PREFERRED EMBODIMENT

Although fiber optical DAS cables are better at detecting axial strain, they can detect radial strain as a result of the Poisson effect. When radial strain is applied to the fiber, the fiber expands in the axial direction or directly induces a radial strain on the fibre leading to a change in refractive index. The amount of axial strain that is induced by the radial strain is determined by the Poisson ratio, which is a material property of the optical fiber. For most materials, the Poisson's ratio is between 0 and 0.5 (although some exotic materials can have negative values). The amount of refractive index change that is induced by radial strain is determined by the strain-optic coefficients.

As a result of the magnitude of the various strain transfer effects, seismic data recorded using a DAS system will contain signals resulting primarily from waves that are in line with the fiber and smaller signals resulting from waves that are incident perpendicular to the fiber. The latter waves give no signal when the wave is incident exactly perpendicular to the fiber and, by continuity, only small signals when the wave is incident at angles near perpendicular. In the case of Poisson's ratio effects, a broadside seismic wave attempts to induce the same axial strain at every point on the fiber. By symmetry, the axial particle motion and hence the movement of impurities that lead to detection in a DAS system, is zero or near-zero. Hence, radial strain transfer in a uniform situation is mainly governed by strain-optic effects.

In some embodiments, the present invention seeks to resolve the parallel and perpendicular components using a novel fiber optic cable deployment and post-processing scheme effectively generating distributed multi-component seismic data. The degree to which radial strain is converted to axial strain in the fiber can be tailored by coating the fiber with materials that have a larger or smaller Young's Modulus or Poisson's ratio.

Figure 1:
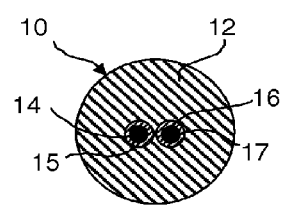
FIG. 1 is a schematic cross-sectional end view showing one embodiment of the invention.

Referring to FIG. 1, a fiber optic cable 10 comprises a sheath 12 containing a first fiber 14 and a second fiber 16. In preferred embodiments of the invention, fibers 14 and 16 are single-mode fibers having different coatings. Preferably, fiber 14 is coated with a coating 15 that minimizes the Poisson's ratio or Young's Modulus of the fiber, while fiber 16 is preferably, but not necessarily, coated with a coating 17 that maximizes its Young's Modulus or Poisson's ratio.

In preferred embodiments, two single-mode fibers 14, 16 are integrated into one cable design. During seismic acquisition, both fibers 14 and 16 are interrogated by the DAS system simultaneously using two interrogators or by connecting the fibres together to form one loop. Because fiber 14 has a minimal radial sensitivity, the signal recorded on this fiber will mainly contain the inline seismic component. The signals recorded on fiber 14 and 16 will contain both inline and broadside components, but in different ratios due to using fibres with different radial sensitivities. By adjusting a portion of the signal from fiber 14 with the same portion of the signal from fiber 16, it is possible to obtain a signal that contains only the broadside component because the common inline component will be cancelled out. These signals are analogous to the "vertical" and "rotated horizontal" components in conventional VSP acquisitions.

In other embodiments, the degree to which radial strain is converted to axial strain in the fiber is tailored by coating the fiber alternately with materials that have larger and smaller Poisson's ratios. In these embodiments of a cable 20, illustrated schematically in FIG. 2, one single-mode fiber 24 is coated such that the Poisson's ratio modulates between high and low values along the length of the fiber, as shown at 26, 28. For the purpose of discussion, two coatings will be described, but it will be understood that any number of types of coating can be used. The variation along the length of the fiber properties breaks the symmetry described above, which would otherwise prevent the detection of a perpendicular, or broadside, wave.

This allows, for example, sections of high Poisson ratio material to expand into neighboring sections with lower Poisson ratio. In detail, a section 28, when hit by a broadside compressional wave in the compression cycle, will contract in the radial direction and as a result expand in the axial direction. This axial expansion will induce contraction in the neighboring sections 26 and the consequent particle motion of the impurities, in both sections 28 and 26, will lead to a measurable signal when interrogated with known fiber optic techniques such as OTDR, even for broadside waves. The coating can be varied between the extremes in any manner that allows better detection of broadside waves, limited only by the expertise and persistence of the manufacturer and the variation can even be continuous and/or random.

Similarly, by axially varying other material properties, such as the Young's modulus (stiffness) of the fiber, along the length of the fiber, it may be possible to induce axial strain modulation in the fiber using a broadside wave. Other properties of the fiber, coating or sheath material can be varied, and may be selected depending on the elasticity, isotropy, and homogeneity of the material(s), including but not limited to the use of metal or gel-filled tubes, polymeric coatings, and other coatings, such as are known in the art.

In preferred embodiments, the heterogeneous fiber with varying Poisson ratio and/or Young's modulus is suspended in a fluid, so that it is not constrained to deform with the formation. The fluid could be water or another incompressible fluid.

Figure 2:
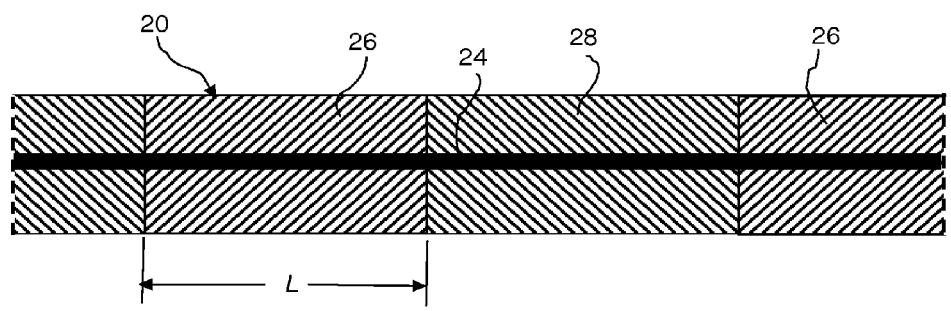
FIG. 2 is a schematic cross-sectional side view showing an alternative embodiment of the invention.

In FIG. 2, the length of each section is shown as L. L is preferably but not necessarily on the same order of magnitude as the spatial resolution of the fiber optic system. If the modulation wavelength L is of the order of the spatial resolution of the DAS system (e.g. 10 m) or bigger, it may be possible to detect alternating signs in the signal as a function of laser-pulse travel time. In this way, broadside waves could be distinguished from waves traveling parallel to the fiber (no modulation of the signal in the latter case). However, if the fiber were suspended in a fluid, the damping effects due to the viscosity of the fluid over distances of about 10 m (relative motion of the fiber with respect to the fiber) might suppress the signal. If the wavelength of the property modulation were much smaller than 10 m, damping effects would be less apparent.

The embodiments described herein can be used advantageously in alone or in combination with each other and/or with other fiber optic concepts. Similarly, the variations described with respect to fiber coatings can be applied using the same principles to the cable jacket including changing properties of a possible gel in the cable.

The methods and apparatus described herein can likewise be used to detect microseisms and the data collected using the present invention, including broadside wave signals, can be used in microseismic localization. In these embodiments, the data are used to generate coordinates of a microseism.

In still other applications, the methods and apparatus described herein can be used to measure arrival times of acoustic signals and in particular broadside acoustic waves. Arrival times give information about the formation and can be used in various seismic techniques.

In still other applications, ability of the present systems to detect broadside waves and axial waves distinguishably can be used in various DAS applications, including but not limited to intruder detection, monitoring of traffic, pipelines, or other environments, and monitoring of various conditions in a borehole, including fluid inflow.

Figure 3:
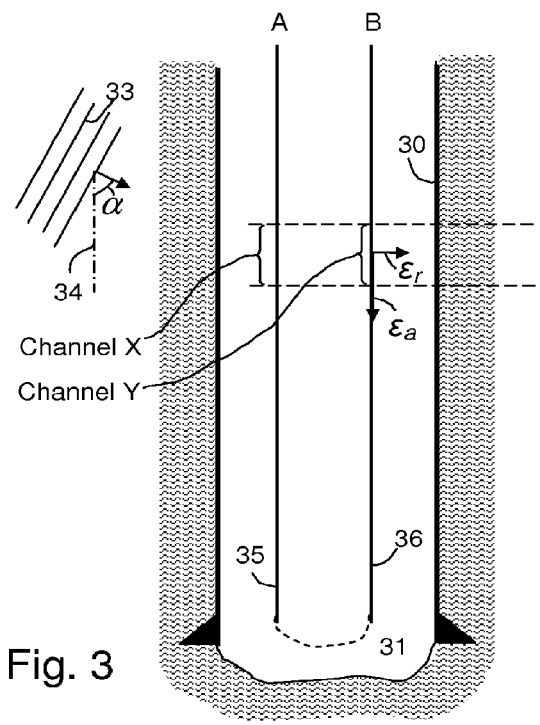
FIG. 3 is a schematic view of a directionally sensitive fiber optical DAS assembly in a well and a graphical and physical explanation of its directional sensitivity.

FIG. 3 is a schematic view of a directionally sensitive fiber optical DAS assembly in a well and a graphical and physical explanation of its directional sensitivity.

FIG. 3 shows two adjacent lengths of optical fiber A and B with different directional acoustic sensitivities in a well 30. The two adjacent lengths of optical fiber A and B may be different fibers that are suspended substantially parallel to each other in the well 30, or may be interconnected by a fiber optical connector 31, or may be different parts of a single U-shaped optical fiber of which the different parts have different directional sensitivities.

To create multi-directional sensitivity, both along cable (axial) and perpendicular to cable (radial) acoustic/strain amplitudes $\epsilon_a$ and $\epsilon_r$ may be detected and processed as shown in Equations (1) and (2).

In FIG. 3 an acoustic wavefront is travelling towards adjacent channels X and Y of the lengths of optical fiber A and B and thereby generate an axial strain $\epsilon_a$ and a radial strain $\epsilon_r$ in these lengths of optical fiber A and B, which axial and radial strains $\epsilon_a$ and $\epsilon_r$ detected by analyzing differences in reflections of optical signals transmitted through the lengths of optical fiber A and B, which reflections stem, on the basis of a time of flight of analysis, from channels X and Y. This can be used: as a "2D" geophone that measures the angle α between the direction of the wavefront 33 and a longitudinal axis 34 of the well 30, or just to improve radial (=broadside) sensitivity, or to determine the angle of incidence α (directivity) of the acoustic wave front 33 relative to the longitudinal axis 34 of the well 30. This requires measuring by at least two lengths of fibre A and B simultaneously. The axial/radial sensitivity ratio of these two fibres should be different. The fibres should be in the same acoustic input wavefront 33 (i.e. close to each other, same coupling, etc.), be it different fibres in one cable assembly or multiple cable assemblies next to each other.

To control the ratio between axial and radial sensitivity $\epsilon_a$ and $\epsilon_r$ of the lengths A and B of optical fibre these lengths may be coated with different coatings. For example, the first length of optical fibre A may be coated with standard acrylate coating 35 whilst the second length of optical fibre B may be coated with a copper coating 36. The difference in Young's Modulus (and to a lower degree: Poisson's ratio), change the degree to which physical length and optical path length (speed of light) vary. This leads to a different ratio between axial and radial sensitivity resulting from different axial and radial strain $\epsilon_a$ and $\epsilon_r$ measured at channels X and Y and other channels along the lengths of optical fiber A and B.

Figure 4:
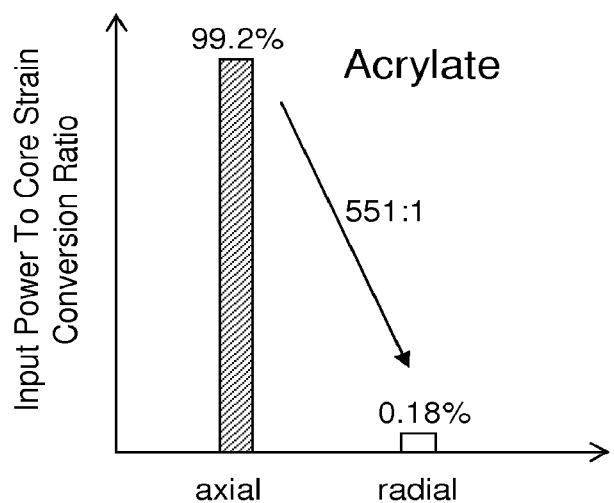
FIGS. 4 and 5 are plots showing exemplary ratios between the axial and radial strain and associated axial and radial acoustic sensitivity for acrylate- and copper-coated optical fibers, respectively.
Figure 5:
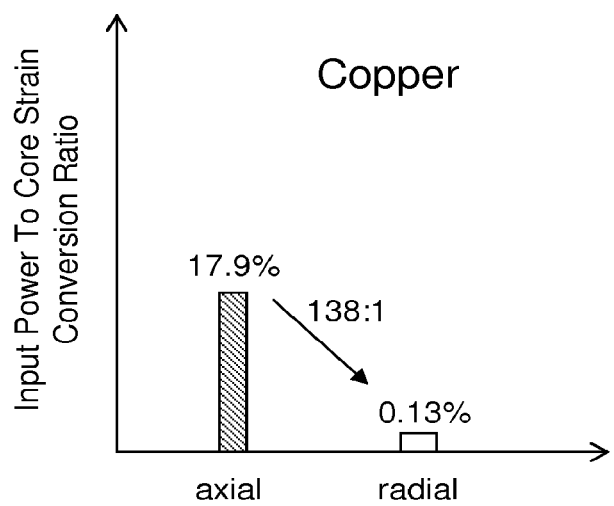

FIGS. 4 and 5 show that the ratio between the axial and radial strain and associated axial and radial acoustic sensitivity of the acrylate coated length of optical fiber A is about 551:1 and that the ratio between the axial and radial strain and associated axial and radial acoustic sensitivity of the copper coated length of optical fiber B is about 138:1. Different alternative coatings 35, 36 may be used, provided that these alternative coatings 35,36 result in different axial and radial acoustic sensitivities of the two lengths of optical fiber A and B, wherein the ratio of the axial and radial acoustic sensitivities of the first length of optical fiber A is preferably in the range between 1 and 300 and the ratio between the axial and radial acoustic sensitivity of the second length of optical fiber B is preferably in the range between 300 and 700.

Equations (1) and (2) show how the directional sensitivities $\Delta \Phi_A^{DAS}$ and $\Delta \Phi_B^{DAS}$ are derived.

$$\Delta \phi_A^{DAS} = f(\epsilon_{axial}^{outside}) + g(\epsilon_{radial}^{outside}) \qquad (1)$$

$$\Delta \phi_B^{DAS} = h(\epsilon_{axial}^{outside}) + k(\epsilon_{radial}^{outside}) \qquad (2)$$

where the axial and radial strains $\epsilon_{axial}$ and $\epsilon_{radial}$, respectively, are measured at the outside of channels X and Y of the adjacent lengths of optical fibre A and B. When the ratio of the axial to radial strain is known for each cable, Equations 1 and 2 can be solved for the strain variables.

The method according to the invention may not only used a) to control this axial/radial strain ratios $\epsilon_a$/and $\epsilon_r$ of the adjacent lengths of optical fibre A and B but also b) for simply improving radial (=broadside) sensitivity resulting from radial strain $\epsilon_r$.

It will be understood that the objectives a) and b) may not only be achieved by providing the adjacent lengths of optical fiber with different fibre coatings, such as acrylate and copper, but can also be achieved by providing the adjacent lengths of optical cable A and B with different properties, such as different Young's Modulus of any fibre layers, different diameters of fibre (layers), different properties of fillings (like gel) used in cable assemblies, for example different viscosity and Young's Modulus of such gels, different materials and thicknesses used for metal tubes in cable assemblies and/or alternating properties along the lengths of optical fibre A and B of the fiber optical DAS assembly according to the invention.

EXAMPLE

In a hypothetical example, a first cable segment A includes an outer shell constructed of PVC, which is relatively stiff (Young's modulus 3 GPa) and quite light. Between the PVC and the cable, is left empty. Strains in the formation will not be effectively transferred to the cable in this segment, so it represents the part of the cable with a "low Poisson's Ratio" coating. In another segment of the same cable, B, the cable is embedded in rubber, which has a very high Poisson's ratio and is very compressible. If it were sufficiently bonded to the cable, the rubber would be expected to cause significant axial strain on the cable when impacted by a broadside wave. The PVC can be installed in the field from two halves with watertight caps on the ends allowing the cable to pass through. The entire composite cable is preferably placed in a trench and water would be added so that it would end up encased in ice (Y=9 GPa), or other suitable material, such as cement, so as to ensure good coupling to the earth. The total length could be a up to several hundred meters.

In another hypothetical example, a first cable is combined with a second, similar cable, in which the second cable is acoustically isolated from the formation. Using techniques described above, the data from the two cables can be resolved into inline and broadside signals. One technique for isolating the second cable includes the use of a PVC outer shell with an airspace between the shell and the fiber. The properties of each fiber could be modulated along its length.

In still another embodiment, a single cable may be coupled to the formation using different materials along its length. For example, a cable may be embedded in ice or cement along one portion of its length and in earth along another portion of its length. In a particular embodiment two adjacent and parallel portions of a cable may be coupled using different materials and the signals from the two cable portions can be processed as described above.

While preferred embodiments have been disclosed and described, it will be understood that various modifications can be made thereto.

The invention claimed is:

1. A Distributed Acoustic Sensing (DAS) fiber optical assembly comprising at least two lengths of adjacent optical fiber with different directional acoustic sensitivities wherein the at least two lengths of adjacent optical fiber comprise a first length of optical fiber with a first ratio between its axial and radial acoustic sensitivity and a second length of optical fiber with a second ratio between its axial and radial acoustic sensitivity, wherein the second ratio is different from the first ratio.

2. The DAS assembly of claim 1, wherein the first ratio is between 100 and 300 and the second ratio is between 300 and 700.

3. The DAS assembly of claim 1, wherein the at least two lengths of adjacent optical fiber comprise a first length of coated fiber having a first coating and a second length of coated fiber having a second coating, wherein the first and second coatings are selected such that one of the Young's Modulus and the Poisson's ratio of the first length of coated fiber is less than the corresponding property of the second length of coated fiber.

4. The DAS assembly of claim 1, wherein the first length of optical fiber has an acrylate coating and the second length of optical fiber has a copper coating.

5. The DAS assembly of claim 1, wherein the at least two lengths of adjacent optical fiber comprise a first length of optical fiber with a first diameter and a second length of optical fiber with a second diameter.

6. The DAS assembly of claim 1, wherein the at least two lengths of adjacent optical fiber comprise adjacent sections of a single fiber optic cable having a coating with at least one property that varies along the length of the cable, the at least one property being selected from the group consisting of Poisson's ratio and Young's modulus.

7. A directionally sensitive Distributed Acoustic Sensing (DAS) method, the method comprising deploying a DAS fiber optical assembly comprising at least two lengths of adjacent optical with different directional acoustic sensitivities wherein the at least two lengths of adjacent optical fiber comprise a first length of optical fiber with a first ratio between its axial and radial acoustic sensitivity and a second length of optical fiber with a second ratio between its axial and radial acoustic sensitivity, wherein the second ratio is different from the first ratio.

8. The method of claim 7, wherein the method is used for creating an image of a subsurface and comprises the steps of:
   a) deploying a fiber optic cable comprising a first fiber having a first coating and a second fiber having a second coating, wherein the first and second coatings are selected such that the Poisson's ratio of the first coated fiber is less than the Poisson's ratio of the second coated fiber;
   b) transmitting a seismic signal into the subsurface;
   c) recording a first data set on the first fiber and a second data set on the second fiber, said data sets including signals received as a result of the seismic signal in step b);
   d) adjusting at least a portion of the first data set with at least a portion of the second data set so as to obtain an output data set that is indicative of portions of received signals travelling through the subsurface in an axial and radial direction with respect to the cable;
   e) using the output data set to create an image of the subsurface.

9. The method according to claim 8 wherein step a) comprises deploying the cable in a deviated borehole.

10. The method according to claim 9 wherein a portion of the borehole is deviated at least 45 degrees from vertical and at least a portion of the cable is deployed in the deviated portion.

11. The method of claim 8 wherein at least one coating has at least one property that varies along the length of the cable, the at least one property being selected from the group consisting of Poisson's ratio and Young's modulus.

12. The method of claim 7, wherein the first ratio is between 1 and 300 and the second ratio is between 300 and 700.

13. The method of claim 7, wherein the first ratio is between 100 and 300 and the second ratio is between 300 and 700.

14. The method of claim 7, wherein the first length of optical fiber has an acrylate coating and the second length of optical fiber has a copper coating.

15. The method of claim 1, wherein the first ratio is between 1 and 300 and the second ratio is between 300 and 700.

* * * * *